United States Patent
Berlin et al.

(10) Patent No.: US 7,534,570 B2
(45) Date of Patent: *May 19, 2009

(54) METHOD FOR THE DETECTION OF CYTOSINE METHYLATIONS IN IMMOBILIZED DNA SAMPLES

(75) Inventors: Kurt Berlin, Stahnsdorf (DE); Matthias Ballhause, Berlin (DE); David Gütig, Berlin (DE)

(73) Assignee: Epigenomics AG, Berlin (DE)

( * ) Notice: Subject to any disclaimer, the term of this patent is extended or adjusted under 35 U.S.C. 154(b) by 0 days.

This patent is subject to a terminal disclaimer.

(21) Appl. No.: 11/981,357

(22) Filed: Oct. 31, 2007

(65) Prior Publication Data

US 2008/0113379 A1    May 15, 2008

Related U.S. Application Data

(63) Continuation of application No. 10/416,624, filed on Jan. 5, 2004, now Pat. No. 7,407,749.

(30) Foreign Application Priority Data

Oct. 26, 2001    (DE) ................. 101 54 317

(51) Int. Cl.
*C12Q 1/68* (2006.01)
*C12P 19/34* (2006.01)

(52) U.S. Cl. .......................... 435/6; 435/91.2
(58) Field of Classification Search ............... 435/6, 435/91.2
See application file for complete search history.

(56) References Cited

U.S. PATENT DOCUMENTS

| 6,214,556 | B1 | 4/2001 | Olek et al. |
| 6,291,166 | B1 | 9/2001 | Gerdes et al. |
| 2004/0054162 | A1 | 3/2004 | Hanna |
| 2004/0152080 | A1 | 8/2004 | Berlin |
| 2004/0241704 | A1 | 12/2004 | Markert-Hahn et al. |

FOREIGN PATENT DOCUMENTS

| WO | WO 00/44934 A2 | 8/2000 |
| WO | WO 2005/021563 A2 | 3/2005 |
| WO | WO 2005/021778 A2 | 3/2005 |
| WO | WO 2005/021802 A2 | 3/2005 |
| WO | WO 2005/038051 A2 | 4/2005 |

OTHER PUBLICATIONS

Grunau et al., "Bisulfite genomic sequencing: systematic investigation of critical experimental parameters," Nucleic Acids Research, 2001, 29(13):e65 (1-7).
Gonzalgo et al., "Rapid quantitation of methylation differences at specific sites using methylation-sensitive single nucleotide primer extension (Ms-SNuPE)," Nucleic Acids Research, 25(12):2529-31 (1997).
Rein et al., "Identifying 5-methylcytosine and related modifications in DNA genomes," Nucleic Acids Research, 26(10):2255-64 (1998).
Shepherd et al., "Monitoring of fluorescence during DNA melting as a method for discrimination and detection of PCR products in variety identification," Molecular Breeding 4:509-17 (1998).
Myohanen et al., "Automated fluorescent genomic sequencing as applied to the methylation analysis of the human ornithine decarboxylase gene," DNA Sequence—The Journal of Sequence and Mapping, 5:1-8 (1994).
Meissner et al., "Reduced representaion bisulfite sequencing for comparative high-resolution DNA methylation analysis," Nucleic Acids Research, 33(18):5868-77 (2005).
Olek et al., "A modified and improved method for busulphite based cytosine methylation analysis," Nucleic Acids Research, 24(24):5064-6 (1996).

*Primary Examiner*—Kenneth R. Horlick
(74) *Attorney, Agent, or Firm*—Kriegsman & Kriegsman

(57) ABSTRACT

A method is described for the analysis of cytosine methylation patterns in genomic DNA samples. In the first method step, the genomic DNA is isolated from cells or other accompanying materials and bound essentially irreversibly to a surface. Then the DNA bound to the surface is treated, preferably with a bisulfite, in such a way that cytosine is converted into a base that is different in its base pairing behavior in the DNA duplex, while 5-methylcytosine remains unchanged. Then the reagents that were used are removed in a washing step. Finally, selected segments of the immobilized DNA are amplified in a polymerase reaction and the amplified products are investigated with respect to their sequence.

10 Claims, No Drawings

METHOD FOR THE DETECTION OF CYTOSINE METHYLATIONS IN IMMOBILIZED DNA SAMPLES

CROSS-REFERENCE TO RELATED APPLICATIONS

The present application is a continuation of U.S. patent application Ser. No. 10/416,624, filed Jan. 5, 2004, now U.S. Pat. No. 7,407,749, the disclosure of which is incorporated herein by reference.

FIELD OF THE INVENTION

The present invention concerns a method for the detection of cytosine methylation in DNA samples.

The levels of observation that have been well studied in molecular biology according to developments in methods in recent years include the genes themselves, the transcription of these genes into RNA and the translation to proteins therefrom. During the course of development of an individual, which gene is turned on and how the activation and inhibition of certain genes in certain cells and tissues are controlled can be correlated with the extent and nature of the methylation of the genes or of the genome. In this regard, pathogenic states are also expressed by a modified methylation pattern of individual genes or of the genome.

5-Methylcytosine is the most frequent covalently modified base in the DNA of eukaryotic cells. For example, it plays a role in the regulation of transcription, in genetic imprinting and in tumorigenesis. The identification of 5-methylcytosine as a component of genetic information is thus of considerable interest. 5-Methylcytosine positions, however, cannot be identified by sequencing, since 5-methylcytosine has the same base-pairing behavior as cytosine. In addition, in the case of a PCR amplification, the epigenetic information which is borne by the 5-methylcytosines is completely lost.

A relatively new method that in the meantime has become the most widely used method for investigating DNA for 5-methylcytosine is based on the specific reaction of bisulfite with cytosine, which, after subsequent alkaline hydrolysis, is then converted to uracil, which corresponds in its base-pairing behavior to thymidine. In contrast, 5-methylcytosine is not modified under these conditions. Thus, the original DNA is converted so that methylcytosine, which originally cannot be distinguished from cytosine by its hybridization behavior, can now be detected by "standard" molecular biology techniques as the only remaining cytosine, for example, by amplification and hybridization or sequencing. All of these techniques are based on base pairing, which is now fully utilized. The prior art, which concerns sensitivity, is defined by a method that incorporates the DNA to be investigated in an agarose matrix, so that the diffusion and renaturation of the DNA is prevented (bisulfite reacts only on single-stranded DNA) and all precipitation and purification steps are replaced by rapid dialysis. (Olek A, Oswald J, Walter J. A modified and improved method for bisulphite based cytosine methylation analysis. Nucleic Acids Res. 1996 Dec. 15;24(24):5064-6). Individual cells can be investigated by this method, which illustrates the potential of the method. Of course, up until now, only individual regions of up to approximately 3000 base pairs long have been investigated; a global investigation of cells for thousands of possible methylation analyses is not possible. Of course, this method also cannot reliably analyze very small fragments of small quantities of sample. These are lost despite the protection from diffusion through the matrix.

An overview of other known possibilities for detecting 5-methylcytosines can be derived from the following review article: Rein T, DePamphilis M L, Zorbas H. Identifying 5-methylcytosine and related modifications in DNA genomes. Nucleic Acids Res. 1998 May 15;26(10):2255-64.

The bisulfite technique has been previously applied only in research, with a few exceptions (e.g., Zeschnigk M, Lich C, Buiting K, Dörfler W, Horsthemke B. A single-tube PCR test for the diagnosis of Angelman and Prader-Willi syndrome based an allelic methylation differences at the SNRPN locus. Eur J Hum Genet. 1997 March-April; 5(2):94-8). However, short, specific segments of a known gene have always been amplified after a bisulfite treatment and either completely sequenced (Olek A, Walter J. The pre-implantation ontogeny of the H19 methylation imprint. Nat. Genet. 1997 November; 17(3):275-6) or individual cytosine positions have been detected by a "primer extension reaction" (Gonzalgo M L, Jones P A. Rapid quantitation of methylation differences at specific sites using methylation-sensitive single nucleotide primer extension (Ms-SNuPE) Nucleic Acids Res. 1997 Jun. 15;25(12):2529-31, WO Patent 95-00669) or an enzyme cleavage (Xiong Z, Laird P W COBRA: a sensitive and quantitative DNA methylation assay. Nucleic Acids Res. 1997 Jun. 15;25(12):2532-4). Detection by hybridization has also been described (Olek et al., WO-A 99-28498).

Urea improves the efficiency of bisulfite treatment prior to sequencing of 5-methylcytosine in genomic DNA (Paulin R, Grigg G W, Davey M W, Piper A A. Urea improves efficiency of bisulphite-mediated sequencing of 5'-methylcytosine in genomic DNA. Nucleic Acids Res. 1998 Nov. 1;26(21):5009-10).

Other publications which are concerned with the application of the bisulfite technique for the detection of methylation in the case of individual genes are: Grigg G, Clark S. Sequencing 5-methylcytosine residues in genomic DNA. Bioassays. 1994 June; 16(6):431-6, 431; Zeschnigk M, Schmitz B, Dittrich B, Buiting K, Horsthemke B, Dörfler W. Imprinted segments in the human genome: different DNA methylation patterns in the Prader-Willi/Angelman syndrome region as determined by the genomic sequencing method. Hum Mol. Genet. 1997 March; 6(3):387-95; Feil R, Chariton J, Bird A P, Walter J, Reik W. Methylation analysis on individual chromosomes: improved protocol for bisulphite genomic sequencing. Nucleic Acids Res. 1994 Feb. 25;22(4):695-6; Martin V, Ribieras S, Song-Wang X, Rio M C, Dante R. Genomic sequencing indicates a correlation between DNA hypomethylation in the 5' region of the pS2 gene and in its expression in human breast cancer cell lines. Gene. 1995 May 19;157(1-2):261-4; WO 97/46705, WO 95/15373 and WO 95/45560.

Another known method is so-called methylation-sensitive PCR (Herman J G, Graff J R, Myohanen S, Nelkin B D, Baylin S B (1996), Methylation-specific PCR: a novel PCR assay for methylation status of CpG islands. Proc Natl Acad Sci U S A. September 3;93(18):9821-6). For this method, primers are used which hybridize either only to a sequence that forms by the bisulfite treatment of a DNA which is unmethylated at the respective position, or, vice versa, primers which bind only to a nucleic acid which forms by the bisulfite treatment of a DNA unmethylated at the respective position. Amplified products can be produced accordingly with these primers, the detection of which in turn supplies indications of the presence of a methylated or unmethylated position in the sample to which the primers bind.

A newer method is also the detection of cytosine methylation by means of a Taqman PCR, which has become known as "methyl light" (WO 00/70090). It is possible with this method to detect the methylation state of individual positions or a few positions directly in the course of the PCR, so that a subsequent analysis of the products becomes superfluous.

An overview of the state of the art in oligomer array production can be derived also from a special issue of Nature Genetics which appeared in January 1999 (Nature Genetics Supplement, Volume 21, January 1999), the literature cited therein and U.S. Pat. No. 5,994,065 on methods for the production of solid supports for target molecules such as oligonucleotides in the case of reduced nonspecific background signal.

Probes with multiple fluorescent labels are used for scanning an immobilized DNA array. Particularly suitable for fluorescent labels is the simple introduction of Cy3 and Cy5 dyes at the 5'-OH of the respective probe. The fluorescence of the hybridized probes is detected, for example, by means of a confocal microscope. The dyes Cy3 and Cy5, among many others, are commercially available.

Matrix-assisted laser desorptions/ionization mass spectrometry (MALDI-TOF) is a very powerful development for the analysis of biomolecules (Karas M, Hillenkamp F. Laser desorption ionization of proteins with molecular masses exceeding 10,000 daltons. Anal Chem. 1988 Oct. 15;60(20): 2299-301). An analyte is embedded in a light-absorbing matrix. The matrix is vaporized by a short laser pulse and the analyte molecule is transported unfragmented into the gaseous phase. The analyte is ionized by collisions with matrix molecules. An applied voltage accelerates the ions in a field-free flight tube. Ions are accelerated to varying degrees based on their different masses. Smaller ions reach the detector sooner than large ions.

MALDI-TOF spectroscopy is excellently suitable for the analysis of peptides and proteins. The analysis of nucleic acids is somewhat more difficult (Gut, I. G. and Beck, S. (1995), DNA and Matrix Assisted Laser Desorption Ionization Mass Spectrometry. Molecular Biology: Current Innovations and Future Trends 1: 147-157). For nucleic acids, the sensitivity is approximately 100 times poorer than for peptides and decreases overproportionally with increasing fragment size. For nucleid acids, which have a multiply negatively charged backbone, the ionization process via the matrix is essentially less efficient. In MALDI-TOF spectroscopy, the choice of matrix plays an eminently important role. Several very powerful matrices, which produce a very fine crystallization, have been found for the desorption of peptides. In the meantime, several effective matrices have been developed for DNA, but the difference in sensitivity was not reduced thereby. The difference in sensitivity can be reduced by modifying the DNA chemically in such a way that it resembles a peptide. Phosphorothioate nucleic acids, in which the usual phosphates of the backbone are substituted by thiophosphates, can be converted by simple alkylation chemistry into a charge-neutral DNA (Gut, I. G. and Beck, S. (1995), A procedure for selective DNA alkylation and detection by mass spectrometry. Nucleic Acids Res. 23: 1367-1373). The coupling of a "charge tag" to this modified DNA results in an increase in sensitivity by the same amount as is found for peptides. Another advantage of "charge tagging" is the increased stability of the analysis in the presence of impurities, which make the detection of unmodified substrates very difficult.

Genomic DNA is obtained from DNA of cells, tissue or other test samples by standard methods. This standard methodology is found in references such as Fritsch and Maniatis, Molecular Cloning: A Laboratory Manual, 1989.

After PCR was invented, numerous variants became known in the next few years, which refine this technique for the amplification of DNA. In particular, multiplexing of the PCR (multiplex PCR) should be mentioned here, in which more than 2 specific primers are used and thus a plurality of different, specific amplifications can be produced in one reaction vessel. Particularly interesting also is so-called nested PCR, which is used, among other things, for the detection of particularly small DNA quantities. This type of PCR is comprised of two amplifications, one following the other, wherein the primers of the second amplification lie within the first amplified product and are not identical with the primers of the first amplification. In this way, a particular specificity is achieved, since the primers of the second amplification only function if the intended fragment was produced in the first amplification. In contrast, the propagation of any possible byproducts of the first amplification in the second amplification is excluded as much as possible.

The present methods for methylation analysis, which contain a bisulfite reaction, without exception, have the disadvantage that the reaction solution cannot be utilized directly for a subsequent polymerase chain reaction, since the high salt content of the bisulfite reaction acts in a disruptive manner. Thus, in practice, several purification and/or washing steps must be conducted, which contribute, particularly in the case of small quantities of DNA sample, to the poor reproducibility of the protocols, the troublesome handling and the low sensitivity of the methods. Also, the DNA must first be isolated before it can be utilized in the bisulfite reaction, as is also the case for other molecular biological assays.

The object of the present invention is thus to overcome the disadvantages of the prior art.

The object is solved by a method for the analysis of cytosine methylation patterns in genomic DNA samples, whereby the following method steps are conducted:

a) the genomic DNA is isolated from cells or other accompanying materials and bound essentially irreversibly to a surface;

b) the DNA bound to the surface is treated, preferably with a bisulfite (=disulfite, hydrogen sulfite), in such a way that cytosine is converted into a base that is different in its base pairing behavior in the DNA duplex, while 5-methylcytosine remains unchanged;

c) the reagents used in step b) are removed in a washing step;

d) selected segments of the immobilized DNA are amplified in a polymerase reaction;

e) the amplified products are investigated with respect to their sequence.

It is advantageous if the following additional steps are conducted:

f) the reagents and products of the polymerase reaction are removed in a washing step;

g) other selected segments of the immobilized DNA, which are different from those in step d), are amplified in a polymerase reaction;

h) the amplified products are investigated with respect to their sequence.

In addition, it is particularly advantageous according to the invention that steps f)-g) are repeated several times, whereby in each amplification according to step g), segments other than those in one of the preceding amplifications are amplified.

It is preferred according to the invention that the binding of the DNA to the surface is covalent.

It is particularly advantageous that the DNA is also isolated directly in the immobilization step.

It is preferred according to the invention that the DNA is isolated from whole blood or blood serum. It is also advantageous according to the invention that the DNA is isolated from lysed tissue.

It is thus preferred according to the invention that the lysis is conducted by means of proteinase K.

It is particularly preferred according to the invention that immobilization is conducted in the wells of a microtiter plate with 96 wells or 384 wells, whereby different DNA samples are immobilized in the wells.

It is particularly advantageous according to the invention that the immobilization is conducted in PCR reaction wells, whereby different DNA samples are immobilized in the wells. It is preferred according to the invention that the DNA is immobilized on a metal oxide, preferably aluminum oxide.

The method according to the invention is also advantageous if immobilization is made on a hydrophobic material and the binding is essentially irreversible only under selected buffer conditions.

It is also preferred according to the invention that an amplification step is conducted with several pairs of primers as a multiplex PCR.

It is thus preferred according to the invention that all amplified products of an immobilized DNA sample, or a large portion thereof, are pooled, and thus are jointly introduced to further analysis. A large portion is approximately 50% or more of the amplified products. However, it can also be up to 75% or more.

It is also preferred in the method according to the invention that this further analysis involves the hybridization to an oligonucleotide array or PNA (peptide nucleic acid) array.

It is also preferred according to the invention that the analysis is conducted during the amplification by means of a real-time PCR method.

It is also advantageous according to the invention that the analysis is conducted after the amplification in the same reaction well by plotting a melting-point curve.

It is particularly preferred according to the invention that the analysis is conducted by allele-specific hybridization of oligonucleotides or PNAs (peptide nucleic acids) at the positions to be investigated in the amplified products.

It is further preferred according to the invention that the analysis is conducted by hybridization of oligonucleotide primers and a subsequent primer extension reaction or a sequencing reaction.

The subject of the present invention is also the use of the method according to the invention for the diagnosis and/or prognosis of adverse events for patients or individuals, whereby these adverse events belong to at least one of the following categories: undesired drug interactions; cancer diseases; CNS malfunctions, damage or disease; symptoms of aggression or behavioral disturbances; clinical, psychological and social consequences of brain damage; psychotic disturbances and personality disorders; dementia and/or associated syndromes; cardiovascular disease, malfunction and damage; malfunction, damage or disease of the gastrointestinal tract; malfunction, damage or disease of the respiratory system; lesion, inflammation, infection, immunity and/or convalescence; malfunction, damage or disease of the body as a consequence of an abnormality in the development process; malfunction, damage or disorder of the skin, the muscles, the connective tissue or the bones; endocrine and metabolic malfunction, damage or disease; headaches or sexual malfunction.

The use of a method according to the invention is preferred according to the invention for distinguishing cell types or tissues or for investigating cell differentiation.

The subject of the present invention is also a kit, comprised of a reagent for the treatment of DNA according to step b, at least two primer oligonucleotides for producing the amplified products, a solid phase for immobilizing the sample DNA, as well as, optionally, other solutions, and instructions for conducting an assay according to a method according to the invention.

The solution to the problem which is the basis for the present invention consists of the fact that the DNA, which is bound to a solid phase in the scope of its aimed-at isolation from, for example, whole blood, blood serum or tissue, is also directly subjected to a subsequent bisulfite reaction on this solid phase, without anything further. After the very simple removal of the bisulfite reaction mixture, which can be achieved in this case by post-washing with water or a suitable buffer, the immobilized DNA can be utilized directly also for the amplification. Alternatively, it can be stored in this immobilized form and used for amplification only as needed. Since the immobilized DNA is not substantially changed by the amplification, it is also possible to conduct several subsequent amplifications with the immobilized DNA as a template, after the reaction components of each preceding amplification have been removed by washing steps.

Overall, the present invention thus provides a method, which represents a considerable simplification with respect to conducting any methylation assay based on bisulfite treatment. The sample DNA need only be bound directly to a solid phase; the bisulfite treatment will be conducted on this solid phase and subsequently a polymerase reaction will be conducted also with the use of the same solid phase. This also permits conducting stable assays starting from very small DNA quantities, such as those from blood serum.

In a meaningful way, the solid phase is a modified surface of a well, in which the PCR reaction is then also conducted, and advantageously, a commercially available PCR well, which may also be present as a figure-8 strip or as part of a microtiter plate. The essential object of the present invention was thus to provide surfaces, among other things, which, first of all, can bind the DNA irreversibly as much as possible, and secondly, however, also remain sufficiently stable under the conditions prevailing in the bisulfite treatment and additionally keep the DNA bound.

Two surfaces were identified which fulfill this objective. The first is aluminum oxide, and the second, C18-alkyl chains, which permit solid binding of the DNA in combination with suitable cations, such as triethylammonium ions. C18-alkyl chains can be introduced by means of an octadecyl trialkoxysilane by the silanizing method, which is known by the person of average skill in the art. Methods for modifying surfaces with aluminum oxide are described in U.S. Pat. No. 6,291,166, among other [publications].

The method according to the invention for the analysis of cytosine methylation patterns is comprised of the following substeps:

1. The genomic DNA is isolated from cells or other accompanying materials and bound essentially irreversibly to a surface.
2. The DNA bound to the surface is treated, preferably with a bisulfite (=disulfite, hydrogen sulfite), in such a way that cytosine is converted into a base that is different in its base pairing behavior in the DNA duplex, while 5-methylcytosine remains unchanged.
3. The reagents used in the second step are removed in a washing step.
4. Selected segments of the immobilized DNA are amplified in a polymerase reaction and 5. The amplified products are investigated with respect to their sequence.

In a particularly preferred variant of the method, the following steps are additionally conducted:

6. The reagents and products of the polymerase reaction are removed in a washing step.
7. Other selected segments of the immobilized DNA, which are different from those in step d), are amplified in a polymerase reaction.
8. The amplified products are investigated with respect to their sequence.

In another particularly preferred variant of the method, steps 6-8 are repeated several times.

In the first method step, the preferably genomic DNA is isolated from cells or other accompanying materials and bound essentially irreversibly to a surface.

An irreversible binding in the sense of the present invention means a binding, which cannot be completely separated again with the means usually available under the conditions prevailing in the reaction. This binding may preferably involve a covalent binding, an ion-pair binding, or, however, a binding which is based on electrostatic or hydrophobic effects.

The DNA is preferably isolated in such a way that a body fluid or, however, a lysate of a tissue is contacted with the surface, which in turn preferably binds the DNA irreversibly. A special buffer (for example, triethylammonium acetate) is required for this purpose in the case of the C18 material. The supernatant is removed and it is post-washed either with buffer or water (or both), in order to conduct the subsequent bisulfite reaction with initial material that is as purified as possible.

In a particularly preferred variant of the method, the binding of the DNA to the surface is covalent. In another particularly preferred method variant, the DNA is also isolated directly in the immobilization step. The DNA is preferably isolated from whole blood or blood serum.

In another particularly preferred method variant, the DNA is isolated from lysed tissue. The lysis is particularly preferably conducted by means of proteinase K.

In another particularly preferred method variant, immobilization is conducted in the wells of a microtiter plate with 96 wells or 384 wells, in which different DNA samples are immobilized in the wells.

In a particularly preferred method variant, the immobilization is conducted in PCR reaction wells, whereby different DNA samples are immobilized in the wells.

The DNA is particularly preferably immobilized to a metal oxide, preferably aluminum oxide. In another particularly preferred method variant, the immobilization is made on a hydrophobic material and the binding is essentially irreversible only under selected buffer conditions.

The DNA to be analyzed is obtained preferably from the usual sources for DNA, such as, e.g., cell lines, blood, sputum, stool, urine, cerebrospinal fluid, tissue embedded in paraffin, for example, tissue from eyes, intestine, kidney, brain, heart, prostate, lung, breast or liver, histological slides and all other possible combinations thereof.

In the second step of the method, the DNA bound to the surface is preferably treated with bisulfite (=disulfite, hydrogen sulfite) in such a way that all of the cytosines not methylated at the 5-position of the base are modified such that a base that is different with respect to its base pairing behavior is formed, whereas the cytosines that are methylated in the 5-position remain unchanged.

If a bisulfite reagent is used, trialkylammonium bisulfite is particularly preferred in the case of the C18 surface, in order to assure a solid binding of the DNA to the surface. In the case of the aluminum oxide surface, sodium bisulfite is preferably used.

The DNA sample is particularly preferably denatured prior to the treatment, either thermally or with the use of an alkaline reagent, such as, for example, dilute (preferably 0.1 to 0.3 M) sodium hydroxide.

If bisulfite is used for the reaction, then an addition occurs on the unmethylated cytosine bases. For the method according to the invention, a denaturing reagent or solvent as well as a radical trap are also preferably present.

The following compounds or compound classes are preferably considered as the denaturing reagents or solvents: polyethylene glycol dialkyl ethers, dioxane and substituted derivatives, urea or derivatives, acetonitrile, primary alcohols, secondary alcohols, tertiary alcohols, diethylene glycol dialkyl ethers, triethylene glycol dialkyl ethers, tetraethylene glycol dialkyl ethers, pentaethylene glycol dialkyl ethers, hexaethylene glycol dialkyl ethers, DMSO or THF. Of course, the DNA may also be embedded in agarose after the denaturing, by adding the agarose in dissolved form and subsequent cooling, analogous to the method published by Olek et al. The agarose can be removed thermally after the bisulfite treatment with hot buffer or hot water.

The subsequent alkaline hydrolysis (preferably: Tris buffer pH 10 or ammonia) then leads to the conversion of unmethylated cytosine nucleobases to uracil. After this, the desulfonation of the DNA (10-30 min, 90-100° C.) at alkaline pH is then preferably conducted.

In the third step of the method, the previously used reagents are removed in a washing step. It is again important that the immobilized, now chemically treated DNA that is present remains bound to the surface. This is simple in the case of a covalent binding, for example, at the surface. In contrast, an appropriate buffer is necessary, if binding has been produced, for example, via triethylammonium cations to a C18 phase. The latter also requires a buffer which promotes the binding of the DNA to the hydrophobic phase, such as, for example, a triethylammonium acetate buffer, in the washing steps.

Preferably, several washing steps are conducted, which are particularly preferably comprised of an automated pipetting step, in which water or buffer is added, and a subsequent pipetting step, in which the respective buffer or the water is again removed. This can be done, for example, by an immobilization of the DNA in a microtiter plate and with the use of a commercially available pipetting robot (e.g., made by the companies Tecan or Qiagen).

In the fourth step of the method, selected segments of the immobilized, treated DNA are amplified.

The DNA sample is amplified in a polymerase chain reaction, preferably with a heat-stable DNA polymerase. The amplification of several DNA segments is preferably conducted in one reaction vessel or well.

The method step also can preferably be carried out in two substeps. One begins with a PCR pre-amplification with at least one pair of primers of different sequence, which nonspecifically hybridize the pretreated DNA sample and thus more than one amplified product results in the PCR step. Then a PCR amplification of the product formed in the pre-amplification is conducted with primers of different sequence, which are each identical or inversely complementary to a segment of the pretreated DNA sample [(+) strand or (−) strand], and which hybridize specifically to the DNA to be amplified.

In a particularly preferred variant of the method, an amplification step is conducted with several pairs of primers as a multiplex PCR. It is also particularly preferred that all amplified products of an immobilized DNA sample, or a large portion thereof, are pooled, and thus are jointly introduced to further analysis. After the amplification, it is particularly preferred to remove the reaction mixture from the reaction vessel or well, to which the immobilized DNA is bound. Thus the immobilized DNA is made available as a template for further amplifications, preferably again with primers that have not been used previously.

In a particularly preferred method variant, the amplification is thus repeated several times with different primers, so that the method has the following additional steps:
1) the reagents and products of the polymerase reaction are removed in a washing step;
2) other selected segments of the immobilized DNA, which are different from those that were previously amplified, are now amplified in a polymerase reaction;
3) the amplified products are investigated with respect to their sequence.

In a particularly preferred variant of the method, these steps are repeated several times, whereby in each amplification according to step 2), segments other than those in one of the preceding amplifications are amplified.

In the last step of the method, and even if the above additional steps are conducted, each of the amplified products is investigated with respect to its sequence. The methylation state of selected cytosine bases in the DNA sample can be directly determined in this way.

This sequence analysis and the subsequent determinations of methylation state can be produced in principle with the use of many methods, which are also described in the prior art and are known by the person of average skill in the art.

Analysis by hybridization of the amplified products on an oligonucleotide array or PNA (peptide nucleic acid) array is particularly preferred It is also preferred that the analysis is conducted during the amplification by means of a realtime PCR method. A variant of the invention in which the extraction of the DNA, the bisulfite treatment, the amplification and the detection, which is preferably performed by means of realtime PCR, thus all of the steps, can be conducted in one reaction vessel or well is particularly preferred. In this connection, a method is also particularly preferred, in which the analysis is conducted after the amplification in the same reaction vessel by the plotting of a melting-point curve and the base composition of the fragment and thus the methylation state can be determined from the melting behavior.

The analysis can also be conducted by introducing the surface into a mass spectrometer, which determines the molecular mass of the amplified products, of fragments of the amplified products, or, however, of probes, which specifically hybridize to the amplified products. This information can be drawn on in turn for identifying sequences if the sequence is already known for the most part. It is also possible to introduce the dissolved amplified products separately into a mass spectrometer and to conduct the analysis according to methods known to the person of average skill in the art.

A method is also particularly preferred, in which the analysis is conducted by allele-specific hybridization of oligonucleotides or PNAs (peptide nucleic acids) at the positions to be investigated in the amplified products.

In another particularly preferred variant of the method, the analysis is conducted by hybridization of oligonucleotide primers and a subsequent primer extension reaction or a sequencing reaction.

The subject of the present invention is also the use of the above-described method for the diagnosis and/or prognosis of adverse events for patients or individuals, whereby these adverse events belong to at least one of the following categories: undesired drug interactions; cancer diseases; CNS malfunctions, damage or disease; symptoms of aggression or behavioral disturbances; clinical, psychological and social consequences of brain damage; psychotic disturbances and personality disorders; dementia and/or associated syndromes; cardiovascular disease, malfunction and damage; malfunction, damage or disease of the gastrointestinal tract; malfunction, damage or disease of the respiratory system; lesion, inflammation, infection, immunity and/or convalescence; malfunction, damage or disease of the body as a consequence of an abnormality in the development process; malfunction, damage or disorder of the skin, the muscles, the connective tissue or the bones; endocrine and metabolic malfunction, damage or disease; headaches or sexual malfunction.

The use of a method is also preferred for distinguishing cell types or tissues or for investigating cell differentiation.

The subject of the present invention is also a kit, comprised of a reagent for the treatment of DNA, at least two primer oligonucleotides for producing the amplified products, a solid phase for immobilizing the sample DNA, as well as, optionally, other solutions, and instructions for conducting at least one of the above-described method variants.

EXAMPLE

Bisulfite treatment of Promega DNA and M13 DNA in derivatized reaction wells

Binding of the DNA

Genomic DNA (Promega) cleaved by EcoRI and M13 plasmid DNA were used for the binding of DNA to the surface of reaction wells coated with aluminum oxide. 160 ng were pipetted each time into the corresponding reaction wells, which were then filled with water to a total volume of 20 µl, mixed briefly on a shaker and incubated for 15 minutes at room temperature. Then the solution was removed and the wells were washed twice, each time with 50 µl of water. In order to reduce the activity of the remaining binding sites on the tube surface, 10 µl of a 5% bovine serum albumin solution were pipetted in, then the well was filled with 40 µl of water and incubation was conducted at room temperature for 15 minutes. Then the wells were washed once with 50 µl of water each.

Bisulfite Treatment

The bound DNA was denatured at 96° C. without addition of water for 20 minutes in an Eppendorf Mastercycler. The wells were then removed as quickly as possible and mixed with 6 µl of dioxane, whereby the DNA remained denatured. For the bisulfite reaction, 10 µl of a 0.75 M sodium bisulfite solution, 2 µl of a radical trap (6-hydroxy-2,5,7,8-tetramethylchromane 2-carboxylic acid, 98.6 mg in 1 ml of dioxane) und 2 µl of water were added. The reaction wells were incubated at 50° C. in an Eppendorf Mastercycler for five hours.

Desulfonation

After the bisulfite reaction was carried out, the solutions were pipetted out and the wells were washed with 100 µl of water and, in preparation for the desulfonation, with 100 µl of a 50 mM Tris-HCl solution. The desulfonation was carried out with 50 µl of a 50 mM Tris-HCl solution at pH 9 for 20 minutes at 96° C. After 3× washing with 50 µl of water each time, the reaction wells were ready for an amplification by means of PCR.

PCR

The PCR was conducted on a scale of 25 µl. The following served as primers for the Promega DNA: 5'-TAA GTA TGT TGA AGA AAG ATT ATT GTA G-3' and 5'-TAA AAA CTA TCC CAT AAT AAC TCC CAA C-3', and the following primers were used for the M13 plasmid DNA: 5'-ATT ACA AAA TCG CGC AAA-3' and 5'-AAG TCG GAG GTT AAA AAG GT-3' (MWG). The two primers were placed each time in a solution with a concentration of 12.5 pmol/µl and 2 µl of this solution of primer pairs were pipetted into the corresponding tube. For the PCR, 2.5 µl of dNTP Mix (Fermentas, concentration of each dNTP: 2.5 µmol/µl), 0.3 µl Hot Star Taq (Qiagen), 2.5 µl 10×PCR Buffer Solution (Qiagen, 15 mmoles of $MgCl_2$ contained in the buffer) and 17.7 µl of water (Fluka) were placed in the wells for each batch.

The PCR was monitored by gel electrophoresis. For this purpose, 5 ul of the sample with 3 µl of loading dye were applied onto a 1.4% agarose gel (Eurogentec, Inc.), and 1×TBE served as the running buffer. The fragments were stained with ethidium bromide and the gel was photographed in UV.

The invention claimed is:

1. A method for the conversion of unmethylated cytosine in genomic DNA samples, said method comprising the steps of:
    a) isolating the genomic DNA from cells or other accompanying materials and essentially irreversibly immobilizing the isolated genomic DNA to a surface, wherein the immobilization is made on a hydrophobic material, and the immobilization is essentially irreversible only under selected buffer conditions;
    b) treating the immobilized DNA with a bisulfite in such a way that cytosine is converted into a base that is different in its base pairing behavior in the DNA duplex, while 5-methylcytosine remains unchanged; and
    c) removing the reagents used in step b) in a washing step.

2. The method according to claim 1, wherein the immobilization of the DNA to the surface is covalent bonding.

3. The method according to claim 1, wherein the DNA is also isolated directly in the immobilizing step.

4. The method according to claim 3, wherein the DNA is isolated from whole blood or blood serum.

5. The method according to claim 3, wherein the DNA is isolated from lysed tissue.

SEQUENCE LISTING

```
<160> NUMBER OF SEQ ID NOS: 4

<210> SEQ ID NO 1
<211> LENGTH: 28
<212> TYPE: DNA
<213> ORGANISM: Homo Sapiens

<400> SEQUENCE: 1
taagtatgtt gaagaaagat tattgtag                                      28

<210> SEQ ID NO 2
<211> LENGTH: 28
<212> TYPE: DNA
<213> ORGANISM: Homo Sapiens

<400> SEQUENCE: 2
taaaaactat cccataataa ctcccaac                                      28

<210> SEQ ID NO 3
<211> LENGTH: 18
<212> TYPE: DNA
<213> ORGANISM: Artificial Sequence
<220> FEATURE:
<223> OTHER INFORMATION: Plasmid DNA

<400> SEQUENCE: 3
attacaaaat cgcgcaaa                                                 18

<210> SEQ ID NO 4
<211> LENGTH: 20
<212> TYPE: DNA
<213> ORGANISM: Artificial Sequence
<220> FEATURE:
<223> OTHER INFORMATION: Plasmid DNA

<400> SEQUENCE: 4
aagtcggagg ttaaaaaggt                                               20
```

6. The method according to claim 5, wherein the lysis is conducted by means of proteinase K.

7. The method according to claim 1, wherein the immobilization is conducted in the wells of a microtiter plate with 96 wells or 384 wells, in which different DNA samples are immobilized in the wells.

8. The method according to claim 1, wherein the immobilization is conducted in PCR reaction wells, whereby different DNA samples are immobilized in the wells.

9. The method according to claim 1, wherein the isolating of the DNA occurs on a metal oxide.

10. A method for the conversion of unmethylated cytosine in genomic DNA samples, said method comprising the steps of:
   a) isolating the genomic DNA from cells or other accompanying materials and essentially irreversibly immobilizing the isolated genomic DNA to a surface, wherein the immobilization is made on a hydrophobic material, and the immobilization is essentially irreversible only under selected buffer conditions;
   b) denaturing the immobilized DNA;
   c) treating the immobilized DNA with a bisulfite in such a way that cytosine is converted into a base that is different in its base pairing behavior in the DNA duplex, while 5-methylcytosine remains unchanged; and
   d) removing the reagents used in step c) in a washing step,
   e) wherein the denaturing step is performed prior to the addition of bisulfite reagent and after having immobilized the DNA to a surface.

* * * * *